United States Patent [19]

Lallement et al.

[11] 4,059,536

[45] Nov. 22, 1977

[54] IMPROVED PROCESS FOR PREPARING SUPERBASIC DETERGENT ADDITIVES

[75] Inventors: Jacques Lallement, Aubervilliers; Guy Parc, Rueil Malmaison; Gabriel de Gaudemaris, Grenoble, all of France

[73] Assignee: Institut Francais du Petrole, Rueil-Malmaison, France

[21] Appl. No.: 562,897

[22] Filed: Mar. 27, 1975

[30] Foreign Application Priority Data

Mar. 29, 1974 France .................................. 74.11255
May 14, 1974 France .................................. 74.16958

[51] Int. Cl.² .............................................. C10M 1/40
[52] U.S. Cl. ..................................... 252/33.3; 252/18; 252/25; 252/33.4
[58] Field of Search ................... 252/33.3, 34, 18, 25, 252/33.4

[56] References Cited

U.S. PATENT DOCUMENTS

| | | | |
|---|---|---|---|
| 3,087,936 | 4/1963 | LeSuer | 252/33.3 |
| 3,400,075 | 9/1968 | Grimm et al. | 252/34 |
| 3,427,245 | 2/1969 | Hotten | 252/34 |
| 3,451,931 | 6/1969 | Kahn et al. | 252/18 X |
| 3,453,212 | 7/1969 | Dorer | 252/18 X |
| 3,471,403 | 10/1969 | LeSuer et al. | 252/18 X |
| 3,515,669 | 6/1970 | LeSuer | 252/18 X |
| 3,609,076 | 9/1971 | Sabol et al. | 252/33.3 |
| 3,671,430 | 6/1972 | Corringer | 252/33.3 |
| 3,779,922 | 12/1973 | LeSuer | 252/34 |
| 3,783,131 | 1/1974 | LeSuer | 252/18 X |
| 3,896,037 | 7/1975 | Dickey | 252/18 X |
| 3,928,216 | 12/1975 | Saunders et al. | 252/18 X |

*Primary Examiner*—Delbert E. Gantz
*Assistant Examiner*—Andrew H. Metz
*Attorney, Agent, or Firm*—Millen & White

[57] ABSTRACT

New superbasic detergent additives are manufactured in two steps. The first step comprises the reaction of a sulfonic acid with an excess of oxide or hydroxide of lithium or group II A metal. The second step consists of carbonating the oxide or hydroxide in excess. The manufacture is conducted in the presence of a polyalkenylsuccinimide-amine salt.

32 Claims, No Drawings

IMPROVED PROCESS FOR PREPARING SUPERBASIC DETERGENT ADDITIVES

The invention concerns new improved super-basic detergent additives for lubricants and their manufacture.

It is known to use alkaline-earth metal sulfonates containing a basicity reserve, in the form of a basic inorganic salt, usually an alkaline-earth metal carbonate colloidally dispersed in the composition, as detergent additives for lubricants. These additives are usually presented as pre-mixtures in mineral oils.

Their use is highly valuable in lubricants for Diesel engines, in which it is important to protect the oil against the detrimental effect of acid gases, for example, sulfurous and/or sulfuric gases produced by the combustion of the sulfur compounds contained in the fuel.

Various methods for preparing these superbasic detergent additives have already been proposed.

Broadly stated, they consist, in a first step, in forming an oil-soluble sulfonic salt of an alkaline-earth metal, usually a neutral calcium or barium sulfonate, by reacting the alkaline-earth metal oxide or hydroxide, for example lime or barium oxide, in excess, with a sulfonic acid; and, in a second step, in neutralizing the largest possible portion of the oxide or hydroxide in excess with carbon dioxide, to form the corresponding carbonate, which is then dispersed by the sulfonate in the colloidal state within the substrate; the un-carbonated fraction of the alkaline-earth metal oxide or hydroxide is then separated from the reaction mixture, usually by filtration.

This is usually carried out in the presence of a solvent which is withdrawn at the end of the reaction.

It is known that, in such a process, it is not possible to carbonate the whole excess of alkaline-earth metal oxide or hydroxide. In effect, when the carbonation reaction is continued beyond a certain stage of progress, depending on the operating conditions and the composition of the reaction medium, partial or total re-precipitation of the colloidal alkaline-earth metal carbonate takes place, in the form of a fine suspension which cannot be filtered easily, and specially results in a considerable decrease or nullification of the base number of the final product.

In the most favorable cases, carbonation must be stopped when about 70% of the excess of alkaline-earth metal oxide or hydroxide has reacted with carbon dioxide. Usually, this proportion is only 40 to 50%.

We have now found a process which permits a substantial improvement in the utilization rate of the excess of alkaline-earth metal oxide or hydroxide. The super-basic detergent additives which can be prepared according to this process will thus present an increased basicity reserve, for a given amount of oxide or hydroxide.

An object of the invention is to provide an improved process for preparing superbasic detergent additives.

Another object is to provide the so-obtained improved additives, for example, in the form of concentrates in mineral or synthetic oils, and the lubricating compositions containing these improved additives.

As a rule, the process according to the invention comprises the main steps as hereinbefore stated, and is so characterized that at least one polyalkenylsuccinimideamide salt is introduced into the starting reaction mixture in a proportion as hereinafter defined.

Specifically, the polyalkenylsuccinimideamine salt to be used in the process of the invention has one of the following general formulae:

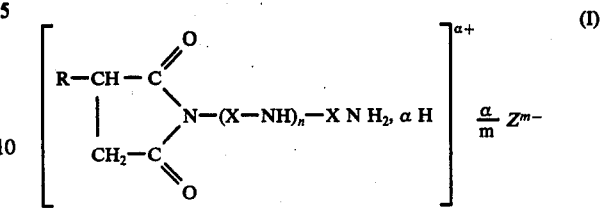

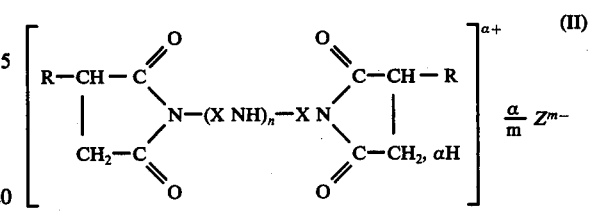

wherein: R is a substantially saturated (i.e. presenting at most a low ethylenic unsaturation) aliphatic hydrocarbon radical; it may be obtained, for example, by polymerization (or copolymerization) of light olefins having, for example, 2–6 carbon atoms, such as ethylene, propylene, 1- and 2-butenes, isobutene or 2-methyl-1-pentene, in the presence of suitable catalysts.

Radical R usually contains 20–250 carbon atoms, specially 50–150 carbon atoms.

X is an alkylene radical of 2–5 carbon atoms whose valences are located on two distinct carbon atoms. Examples of such alkylene radicals are ethylene, propylene and butylene.

$n$ is an integer from 1 to 5, preferably 1 to 3.

Z is the inorganic or organic anionic radical of a protonic acid $ZH_m$ where $m$ is an integer.

$a$ is a number representing the neutralization ratio of the amine groups of the polyalkenylsuccinimide-amines; it is at most $n+1$ in formula (I) and $n$ in formula (II). $a$ is preferably at least 50% of the number of amine groups.

The manufacture of the polyalkenylsuccinimide-amines or bis-polyalkenylsuccinimide-amines is well known by those skilled in the art; it has been described, for example, in the French Pat. Nos. 1,265,085 and 1,422,401.

The manufacture of the polyalkenylsuccinimide-amine salt used according to the invention is advantageously carried out, prior to manufacturing the superbasic additive, by reacting the suitable polyalkenylsuccinimide-amine with an amount of the acid compound $ZH_m$ corresponding to the desired neutralization ratio of the amine groups (preferably the neutralization of 50–100% of the latter).

Examples of useful acid compounds are:

halohydric acids such as for example, HCl HBr;

monocarboxylic acids of 1–24 carbon atoms, such as, for example, formic, acetic, proprionicbutyric, valeric, lauric, stearic, benzoic, phenylacetic and 2-ethyl hexanoic acids;

carboxylic diacids and polyacids such as, for example, adipic, trimethyladipic, azelaic, sebacic and phthalic acids or polyacids obtained by dimerization or trimerization of unsaturated fatty acids, such as oleic and linoleic acids;

polyfunctional compounds having at least one carboxylic acid group, such as lactic, citric, salicylic, anthranilic or monochloracetic acid.

The reaction of neutralization is preferably carried out in a solvent medium. A useful solvent is a fraction of the solvent mixture (light aliphatic alcohol + liquid hydrocarbon) to be used in the manufacture of the superbasic additive. This fraction preferably amounts to 5–30% of the total amount of solvent to be used, as hereinafter defined.

A practical embodiment of the process according to the invention is described hereinafter in greater detail. The operation details are given as exemplification, with the proviso that, in each of the various steps, it is possible to vary the operating conditions to optimize the results, without departing from the scope of the invention.

Whereas the polyalkenylsuccinimide-amine salt has been hereinbefore defined, the other constituents of the starting reaction mixture may be defined as follows:

In the solvent mixture, the light aliphatic monohydric alcohol is usually methanol; it may also be another alcohol, for example isopropanol or n-butanol. The liquid hydrocarbon may consist essentially of aromatic hydrocarbon, usually toluene, or otherwise benzene, xylene or a mixture of several aromatic hydrocarbons, such as, for example, those of the Solvesso(registered trade mark) type. The liquid hydrocarbon may also at least partly consist of an aliphatic or cycloaliphatic hydrocarbon. In that case, by way of example, the following may be used:

aliphatic hydrocarbons of 5–15 carbon atoms, alone or as mixtures;

oil cuts boiling in the gasoline or white-spirit temperature range;

cycloaliphatic hydrocarbons such as, for example, cyclopentane and cyclohexane.

Specific examples of useful oil cuts are the special gasolines E and F which may have been optionally subjected to dearomatization, so as to reduce to less than 5% by volume their aromatics content, and the white-spirit cuts, such as those of the Varsol (registered mark) type, as sold by Esso-Chimie Company, these cuts having been optionally subjected to dearomatization, to reduce to less than 5% by volume their aromatics content.

The solvent mixture has preferably a ratio by volume of the alcohol to the hydrocarbon of about ¼.

The sulfonic acid may consist of at least one natural or synthetic sulfonic acid; many examples of such acids are given in the literature, for example in the U.S. Pat. Nos. 2,695,910, 3,256,186 and 3,446,736.

The mineral or synthetic dilution oil may consist for example, of a light paraffinic or naphthenic mineral oil whose viscosity at 37.8° C is from 80 to 150 SSU, more specially about 100 SSU, or a synthetic oil of the ester, polyglycol, polyolefine or aromatic alkylate type.

The metal of the oxide or hydroxide is selected from lithium or the metals of group IIA of the periodic classification. Calcium and barium oxides and hydroxides are conventionally used. Magnesium oxide or hydroxide may also be utilized.

In addition, the various ingredients mentioned above are commonly used in the following proportions:

The polyalkenylsuccinimide-amine salt is employed, for example, in a molar proportion from 1 to 10%, preferably 2 to 5%, with respect to the sulfonic acid.

The metal oxide or hydroxide is supplied in excess with respect to the sulfonic acid, usually in an amount corresponding to a number of hydroxy groups higher than 1 and ranging up to about 20, per each acid equivalent, the selected proportion being determined by the choice of the total base number to be obtained in the final product.

The dilution oil is utilized in a proportion of 10–90% by weight of the total amount of oil + sulfonic acid. The dilution oil may be supplied after the sulfonic acid, or as a mixture therewith. It may also be added, if desired, in several fractions, one of them being, for example, added only at the end of the manufacture, when the viscosity and/or basicity of the final product is to be adjusted.

The total volume of solvent is, for example, 1 to 10 liters, particularly about 2–3 liters, per kilogram of the total mixture : sulfonic acid + polyalkenylsuccinimide-amine salt + dilution oil.

The first step of the process according to the invention consists in neutralizing the sulfonic acid with metal oxide or hydroxide. It may take place, for example, at a temperature in the range from room temperature to the boiling temperature of the lightest constituent of the reaction mixture (as a rule, a light aliphatic alcohol). The reaction increases the temperature of the mixture and changes its color.

The temperature is then maintained at about 40°–70° C and, at the end of the neutralization reaction, in a second step, the reaction mixture is contacted with gaseous carbon dioxide, either pure or diluted with a gas inert to the carbonation reaction, for example, air or nitrogen, the dilution rate being advantageously 1 volume of carbon dioxide per each 5 to 10 volumes of gaseous mixture, and that, for a sufficient time to carbonate the largest possible part of the excess of metal oxide or hydroxide, the carbonation reaction being discontinued before any carbonate precipitation. As a rule, in the process according to the invention, this precipitation occurs only at a stage of progress of the carbonation reaction higher than 75%, usually 80–95% or more, with respect to the excess of metal oxide or hydroxide.

The carbonation reaction may be carried out by bubbling pure or dilute carbon dioxide through the reaction mixture stirred in a tight vessel under atmospheric pressure. For a good utilization of carbon dioxide, it may be advantageous to recover the effluent gases and to recycle them to the injection point, for example, by means of a recirculation pump.

According to another embodiment, the carbonation reaction is carried out in a tight enclosure, pure or dilute carbon dioxide being then used under a slight superatmospheric pressure, for example 5–10 cm of water, over the reaction mixture maintained under mechanical stirring. In that case the carbonation velocity depends to a large extent, on the stirring in the medium.

When the carbonation is achieved, the reaction mixture is freed of solid particles, for example, by filtration, and the solvent (light alcohol + liquid hydrocarbon) is discharged, for example, by vacuum evaporation.

The superbasic detergent additive is obtained in the form of a concentrate in the dilution oil added at the beginning and eventually at the end of the manufacture.

The superbasic detergent additives obtained according to the invention have a surprisingly high basicity reserve, which may be 40 to 50% higher than that of corresponding detergent additives prepared under the same conditions, but without addition of polyalkenyl-succinimide-amine salt.

They are usefully employed in mineral or synthetic lubricating oils to be used for lubrication of engines, particularly Diesel engines, 2- or 4- stroke gasoline engines and rotative piston engines. They can be added to lubricants in proportions of 0.5 to 25%, preferably 1–10% by weight, with respect to the total weight of lubricants.

The lubricant may also contain, in sufficient amounts, other detergent additives, such as alkyl phenolates, possibly containing sulfur, phosphonates or salicylates, ashless dispersant additives, such as alkenylsuccinimides, antioxidant additives, such as zinc dialkyl- or diaryldithiophosphates, alkylphenols or aromatic amines, or other conventional additives.

The following examples illustrate the invention; they are not intended to limit the scope thereof in any respect.

In these examples, the total base number of the described additives (TBN) has been determined according to the standard method ASTM D 664. It is expressed as the weight of potassium hydroxide per gram of product.

EXAMPLE 1

The following reactants have been prepared separately:

a mixture of 631 g of a synthetic sulfonic acid (acid number : 80.4) and 229 g of mineral oil of 100 SSU viscosity at 37.8° C. The amount of sulfonic acid equals about 0.96 gram-equivalent of acid;

430 g (5.8 moles) of calcium hydroxide of technical grade;

a solvent mixture consisting of 2.25 liters of toluene and 0.75 liter of methanol;

the hydrochloride of a commercially available polyalkenylsuccinimide-amine of the general formula:

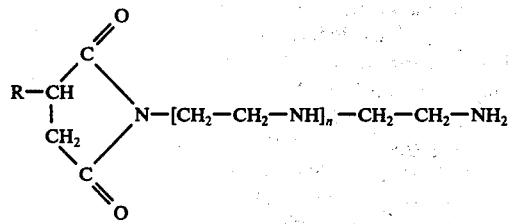

where R is a poly-isobutenyl radical having a molecular weight of 1200 – 1300 and $n$ is 3, i.e. the polyamine group is obtained from tetraethylene pentamine. The commercial product whose total base number is 38.3 consists of 50% b.w dilution of the above polyisobutenylsuccinimide-amine in a lubricating base of low viscosity.

The hydrochloride is prepared by dissolving 140 g of the commercial product, i.e. 70 g of pure polyisobutenylsuccinimide-amine, into 200 ml of the solvent mixture, as hereinbefore defined. The amount of hydrochloric acid (calculated with respect to the total base number) necessary to obtain the desired salt of the polyisobutenylsuccinimide-amine is added under stirring.

The various reactants are introduced into a tight reactor of a 6 liter capacity, provided with a cooler, mechanical stirring means, a carbon dioxide inlet and a differential water manometer. A few moments after stirring has been started, a temperature increase and a color change are observed, corresponding to neutralization of the sulfonic acid. While the temperature is maintained between 50° and 55° C, a continuous carbon dioxide pressure of a few centimeters of water is applied to the reactor. During conversion to carbonate, the absorption of carbon dioxide gas is measured with a volumeter and the operation is discontinued when a volume of gas corresponding to the conversion of 80% of the excess of calcium hydroxide with respect to the carbonate has been consumed. The contents of the reactor are then filtered and the solvent is removed by vacuum evaporation. 1,315 g of oily composition presenting a total base number of 364 is thus obtained.

EXAMPLE 2

The operating conditions are the same as in example 1. The composition and proportions of the reactants are unchanged, except that the polyisobutenylsuccinimide-amine is neutralized with formic acid instead of hydrochloric acid.

An oily composition is obtained whose total base number is 358, the yield being 1,366 g. The carbonation degree of the lime excess was 80%.

EXAMPLE 3

The operating conditions are the same as in example 1, except that acetic acid is used to form the polyisobutenylsuccinimide-amine salt. 1,366 g of an oily composition having a total base number of 354 is thus obtained. The carbonation degree of the lime excess was 80%.

EXAMPLE 4

In this operation, lauric acid is used to form the polyisobutenylsuccinimide-amine salt, the operating conditions being otherwise identical to those of the above examples. 1,348 g of an oily composition having a total base number of 348 is thus obtained. The carbonation degree of the lime excess was 80%.

EXAMPLE 5

This operation is identical to that described in the above examples, except that 2-ethylhexanoic acid is used to salify the polyisobutenylsuccinimide-amine. The resulting oily composition amounted to 1,325 g; it had a total base number of 360. The carbonation degree of the lime excess was 80%.

EXAMPLE 6

The operating conditions are the same as in the above examples. The composition and proportions of reactants are unchanged, as concerns the mixture of sulfonic acid and mineral oil and the solvent mixture. The salt is now the acetic acid salt of a commercial bis (polyisobutenyl-succinimide-amine of the general formula:

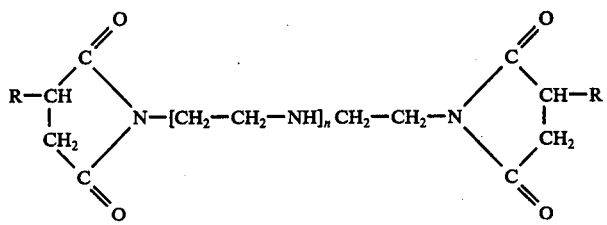

where R, as in example 1, is a polyisobutenyl radical whose molecular weight is 1200–1300, and $n$ is 3 (the polyamine group is that of tetraethylene pentamine). The commercial product, whose total base number is 20.3, consists of a 50% by weight dilution of the above bis(polyisobutenylsuccinimide) in mineral oil of low viscosity. The acetic acid salt is prepared in 200 ml of the solvent mixture of toluene and methanol, by adding to 140 g of the commercial product the theoretical amount of acetic acid, calculated with respect to the total base number, necessary to obtain the desired acetate. The amount of calcium hydroxide to be used is 614 g (8.3 moles), and carbonation is continued up to 85% of the theoretical amount necessary to neutralize the calcium hydroxide excess. 1,486 g of an oily composition having a total base number of 438 is thus obtained.

EXAMPLE 7

The following reactants are prepared separately:

a mixture of 631 g of synthetic sulfonic acid (acid number : 80.4) and 229 g of mineral oil of viscosity 100 SSU at 37.8° C;

400 g (5.4 moles) of calcium hydroxide of technical grade;

a solvent mixture composed of 0.5 liter methanol and 1.5 liter dearomatized white-spirit, as sold by Esso-Chimie under the registered trade mark Varsol;

the acetic acid salt of bis-polyalkenylsuccinimide-amine of commercial grade, as used in example 6.

The acetic acid salt is prepared by adding the theoretical amount of acetic acid (calculated with respect to the total base number) necessary to obtain the desired acetate, to 140 g of the commercial product in 200 ml of a solvent mixture of white-spirit and methanol. The operation is continued as in the preceding examples, and the carbonation reaction is discontinued when the volume of consumed gas corresponding to the carbonation of 85% of the calcium hydroxide excess.

The contents of the reactor are then filtered, and the solvent is removed by vacuum evaporation. 1279 g of oily composition having a total base number (TBN) of 340 is obtained.

EXAMPLE 8 (comparison)

The procedure is the same as in examples 1 to 5, except that no polyalkenylsuccinimide-amine salt is added to the reaction mixture. Calcium carbonate has settled at a carbonation ratio of 70%.

By discontinuing carbonation at a ratio of about 65%, the resulting oily additive composition has a total base number (TBN) of 221 only, far lower than that of the products obtained according to examples 1–5.

TESTS 1–4

The detergency efficiency of additives according to the invention has been checked by testing additives prepared as described in examples 1, 2, 3 and 6 on a Petter AV 1 engine, according to AT 4 method. These additives have been used in a proportion of 3.5% by weight in 200 Neutral mineral oil containing 1% by weight of antioxidant additives. The results of these tests are given in table I hereunder, wherein the highest merit of the various elements of the piston has been noted 10 and the highest merit of the whole piston 80.

These results show the good detergency properties of the additives, as obtained according to the invention.

TABLE I

| Test No. | 1 | 2 | 3 | 4 |
|---|---|---|---|---|
| detergent additive | additive of Ex. 1 | additive of Ex. 2 | additive of Ex. 3 | additive of Ex. 6 |
| ring freedom | 10 | 10 | 10 | 10 |
| crown | 9.1 | 9.2 | 8.7 | 9.1 |
| piston bottom AT 4 | 5.7 | 6.7 | 6.5 | 6.5 |
| skirt after washing | 10 | 10 | 10 | 10 |
| average cordon carbon in the grooves (average) | 7.5 | 7.6 | 7.7 | 9.4 |
|  | 9.9 | 9.8 | 9.9 | 10 |
| varnish in the grooves average scraper ring | 9.0 | 9.1 | 9.5 | 9.6 |
| obstruction | 10 | 10 | 10 | 10 |
| general merit piston/80 | 71.2 | 72.4 | 72.3 | 74.6 |

What we claim is:

1. In a process for preparing a superbasic detergent additive that comprises (a) contacting sulfonic acid with an excess of oxide or hydroxide of a metal element selected from the group consisting of lithium and a metal of Group IIA of the Periodic Classification for a time sufficient to form the sulfonic salt of said metal element, (b) contacting the reaction mixture from step (a) with an amount of carbon dioxide sufficient and at a temperature sufficient to carbonate a substantial portion of the excess amount of said oxide or hydroxide, and (c) separating the uncarbonated fraction of said oxide or hydroxide from the reaction mixture, wherein the improvement comprises employing in the reaction mixture of steps (a), (b) and (c) at least one salt of the formula

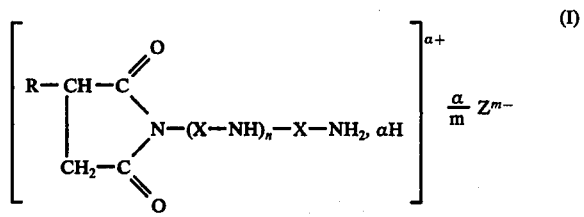

or

-continued

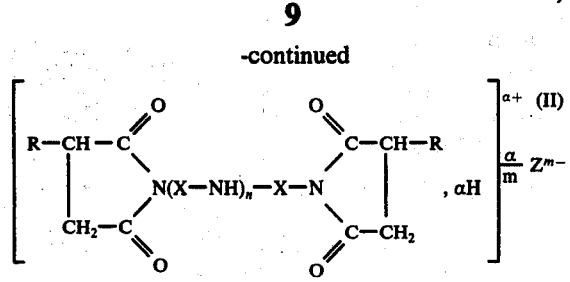

where R is a substantially saturated aliphatic hydrocarbon radical containing from 20 to 250 carbon atoms, X is an alkylene radical of 2–5 carbon atoms, the valences of which are located on separate carbon atoms, n is an integer from 1 to 5, $Z^{m-}$ represents the anion of a protonic acid selected from the group consisting of a halohydric acid, a hydrocarbyl monocarboxylic acid of 1–24 carbon atoms, a hydrocarbyl dicarboxylic acid and a hydrocarbyl polycarboxylic acid, m being the number of acid groups of said protonic acid and a, which represents the number of salified amine groups per molecule of salt, has a value of at most $n+1$ in formula (I) and n in formula (II) said salt being present in sufficient amount to increase the utilization ratio of said excess amount of said oxide or hydroxide.

2. A process according to claim 1, wherein at least 50% of the amine groups in the salt are salified.

3. A process according to claim 1, wherein 100% of the amine groups are salified.

4. A process according to claim 1, wherein the salt is supplied in a molar proportion of 1–10% with respect to the sulfonic acid.

5. A process according to claim 1, wherein the amount of oxide or hydroxide corresponds to a number of hydroxy groups per acid equivalent higher than 1 and ranging up to about 20.

6. A process according to claim 1, wherein said metal element is calcium or barium.

7. A process according to claim 1, wherein the first step is carried out at a temperature ranging from room temperature to the boiling temperature of the most volatile constituent present in the reaction mixture.

8. A process according to claim 1, wherein the second step is carried out at a temperature of 40° to 70° C.

9. A superbasic detergent additive, obtained by the process according to claim 1.

10. A process according to claim 1, wherein said salt is formed between a polyalkenylsuccinimide-amine of the formula

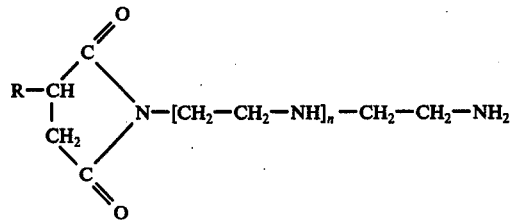

or a polyalkenylsuccinimide-amine of the formula

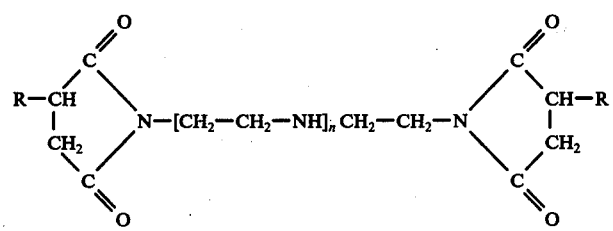

where, R is a poly-isobutenyl radical having a molecular weight of 1200–1300 and n is 3, and a protonic acid selected from the group consisting of hydrochloric acid, formic acid, acetic acid, 2-ethyl hexanoic acid and lauric acid.

11. A process according to claim 4, wherein the molar proportion of the polyalkenylsuccinimide-amine salt with respect to the sulfonic acid is from 2 to 5%.

12. In a process for preparing a superbasic detergent additive that comprises (a) contacting sulfonic acid in a diluent oil which is a mineral oil or a synthetic oil of the ester, polyglycol, polyolefin or aromatic alkylate type, with an excess of oxide or hydroxide of a metal element selected from the group consisting of lithium and a metal of Group II A of the Periodic Classification, in the presence of a solvent system comprising a light aliphatic monohydric alcohol selected from the group consisting of methanol, isopropanol or n-butanol, and a liquid hydrocarbon selected from the group consisting of an aromatic hydrocarbon, a mixture of aromatic hydrocarbons, an aliphatic hydrocarbon of 5–15 carbon atoms, an oil cut boiling in the gasoline or white-spirit temperature range and a cycloaliphatic hydrocarbon, for a time sufficient to form the sulfonic salt of said metal element, (b) contacting the reaction mixture from step (a) with an amount of carbon dioxide sufficient and at a temperature sufficient to carbonate a substantial portion of the excess amount of said oxide or hydroxide without precipitating the carbonated product; (c) separating the uncarbonated fraction of said oxide or hydroxide from the reaction mixture; and (d) removing the volatile solvent components, wherein the improvement comprises employing in the reaction mixture of steps (a), (b), (c) and (d) at least one salt of the formula

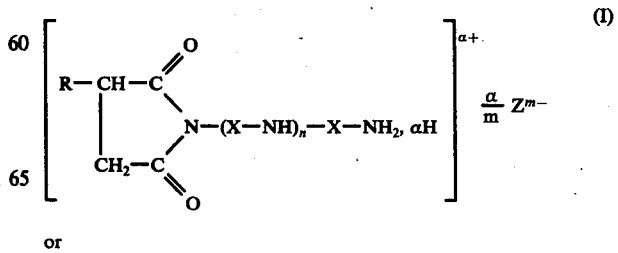

or

-continued

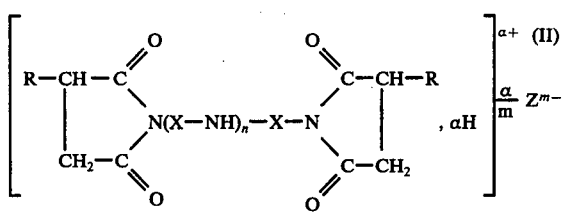

where R is a substantially saturated aliphatic hydrocarbon radical containing from 20 to 250 carbon atoms, X is an alkylene radical of 2–5 carbon atoms the valences of which are located on separate carbon atoms, $n$ is an interger from 1 to 5, $Z^{m-}$ represents the anion of a protonic acid selected from the group consisting of a halohydric acid, a hydrocarbyl monocarboxylic acid of 1–24 carbon atoms, a hydrocarbyl dicarboxylic acid, and a hydrocarbyl polycarboxylic acid, $m$ being the number of acid groups of said protonic acid and $a$, which is the number of amine groups salified in each salt molecule has a positive value of at most $n+1$ in formula (I) and $n$ in formula (II), said salt being present in sufficient amount to increase the utilization ratio of said excess amount of said oxide or hydroxide.

13. An oily concentrate of superbasic detergent additive obtained by the process of claim 12.

14. A process according to claim 12, wherein the salt is supplied in a molar proportion of 1–10% with respect to said sulfonic acid, the temperature in step (a) ranges from room temperature to the boiling temperature of the most volatile component of the reaction mixture, and the temperature in step (b) is from 40° to 70° C.

15. A process according to claim 14, wherein the mineral or synthetic oil is used in an amount of 10–90% by weight of the total amount of oil and sulfonic acid.

16. A process according to claim 14, wherein the volume of said solvent system is 1–10 liters per kilogram of of the total mixture : sulfonic acid + salt + mineral or synthetic oil.

17. A process according to claim 14, wherein the liquid hydrocarbon consists of at least one aromatic hydrocarbon.

18. A process according to claim 14, wherein the liquid hydrocarbon comprises at least one aliphatic or cycloaliphatic hydrocarbon.

19. A lubricating composition comprising a major proportion of at least one mineral or synthetic lubricating oil and a minor proportion of at least one superbasic detergent additive according to claim 13.

20. A lubricating composition according to claim 19, wherein the proportion of superbasic detergent additive amounts to 0.5–25% by weight.

21. A lubricating composition according to claim 19, wherein the proportion of superbasic detergent additive is 1–10% by weight.

22. A process according to claim 14, wherein the diluent oil is a light paraffinic or naphthenic mineral oil having a viscosity at 37.8° C of from 80 to 150 SSU.

23. A process according to claim 17, wherein said aromatic hydrocarbon is toluene.

24. A process according to claim 14, wherein said liquid hydrocarbon is a dearomatized white spirit.

25. A process according to claim 14, wherein said light aliphatic monohydric alcohol is methanol.

26. A process according to claim 14, wherein the volume ratio of said light aliphatic monohydric alcohol to said liquid hydrocarbon is about 1:3.

27. A process according to claim 14, wherein the molar proportion of the salt with respect to the sulfonic acid is from 2 to 5%.

28. A process according to claim 14, wherein up to 75% of the excess amount of metal oxide or hydroxide is carbonated in step (b).

29. A process according to claim 14, wherein up to 80–95% of the excess amount of metal oxide or hydroxide is carbonated in step (b).

30. An additive according to claim 13, having a total base number of from 348 to 364, when calcium hydroxide, a sulfonic acid having an acid number of 80.4, and a mineral diluent oil are used in proportions corresponding to 5.8 moles/0.96 gram-equivalent/229 grams.

31. An additive according to claim 13, having a total base number of 438, when calcium hydroxide, a sulfonic acid having an acid number of 80.4, and a mineral diluent oil are used in proportions corresponding to 8.3 moles/0.96 gram equivalent/229 grams.

32. An additive according to claim 13, having a total base number of 340, when calcium hydroxide, a sulfonic acid having an acid number of 80.4, and a mineral diluent oil are used in proportions corresponding to 5.4 moles/096 gram equivalent/229 grams.

* * * * *